United States Patent [19]
Frei et al.

[11] Patent Number: 5,834,486
[45] Date of Patent: Nov. 10, 1998

[54] PIPERIDINYL-2-ALKYL, SUBSTITUTED LINEAR POLYAMINES FOR THE REDUCTION OF INTRACELLULAR, ENDOGENIC POLYAMINE LEVELS SUCH AS PUTRESCINE, SPERMIDINE AND SPERMINE, AND THEIR IMPACT ON CELL PROLIFERATION

[75] Inventors: Jörg Frei, Hölstein; Jaroslav Stanek, Arlesheim, both of Switzerland

[73] Assignee: Novartis AG, Basel, Switzerland

[21] Appl. No.: 913,367

[22] PCT Filed: Mar. 4, 1996

[86] PCT No.: PCT/EP96/00898

§ 371 Date: Sep. 15, 1997

§ 102(e) Date: Sep. 15, 1997

[87] PCT Pub. No.: WO96/28425

PCT Pub. Date: Sep. 19, 1996

[30] Foreign Application Priority Data

Mar. 15, 1995 [CH] Switzerland ................. 744/95

[51] Int. Cl.$^6$ ............... A61K 31/445; C07D 211/26; C07D 211/34; C07D 211/60
[52] U.S. Cl. ............... 514/315; 514/316; 546/186; 546/246
[58] Field of Search .................. 514/315, 316; 546/186, 246

[56] References Cited

U.S. PATENT DOCUMENTS

| 2,739,981 | 3/1956 | Szabo ................. 562/607 |
| 3,872,171 | 3/1975 | Cronin ................. 564/506 |
| 4,315,859 | 2/1982 | Nikles ................. 544/113 |
| 4,800,153 | 1/1989 | Morimoto ............. 430/380 |
| 5,209,914 | 5/1993 | Peytavy ............... 423/228 |

FOREIGN PATENT DOCUMENTS

| 270349 | 6/1988 | European Pat. Off. . |
| 349224 | 1/1990 | European Pat. Off. . |
| 495749 | 7/1992 | European Pat. Off. . |
| 495750 | 7/1992 | European Pat. Off. . |
| 558443 | 9/1993 | European Pat. Off. . |
| 2104059 | 3/1983 | United Kingdom . |
| 2104060 | 3/1983 | United Kingdom . |
| 8806641 | 9/1988 | WIPO . |
| 8912119 | 12/1989 | WIPO . |

OTHER PUBLICATIONS

Eur. J. Biochem. vol. 221, pp. 391–398 (1994), He.
J. Med. Chem. vol. 37, pp. 3464–3476 (1994), Bergeron.
Chemical Abstract, vol. 88:104645x, 1978.
Derwent Abstract 94–112033/14, 1994.
Derwent Abstract 91–159968/22, 1991.
Derwent Abstract 88–073078/11, 1988.

*Primary Examiner*—John Kight
*Assistant Examiner*—D. Margaret M. Mach
*Attorney, Agent, or Firm*—Joseph J. Borovian

[57] ABSTRACT

The invention relates to compounds of formula (I)

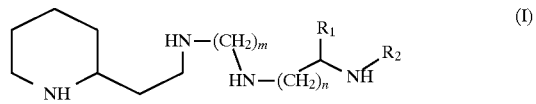

wherein either
  $R_1$ is hydrogen and
  $R_2$ is lower alkyl lower alkenyl or lower alkynyl,
  m is 3 or 4 and
  n is 2 or 3;
or
  $R_1$ and $R_2$ together are tetramethylene,
  m is 3 or 4 and
  n is 2;
or salts thereof.

The compounds of formula (I) influence polyamine biosynthesis and have antiproliferative activity as well as an action against protozoans.

14 Claims, No Drawings

PIPERIDINYL-2-ALKYL, SUBSTITUTED LINEAR POLYAMINES FOR THE REDUCTION OF INTRACELLULAR, ENDOGENIC POLYAMINE LEVELS SUCH AS PUTRESCINE, SPERMIDINE AND SPERMINE, AND THEIR IMPACT ON CELL PROLIFERATION

This application is a 371 of PCT/EP96/00898, filed 4 Mar. 1996.

BRIEF DESCRIPTION OF THE INVENTION

The invention relates to novel cyclic polyamine analogues that are derivatives of propane- or butane-diamine, and to salts thereof, to processes for the preparation of those compounds, to pharmaceutical compositions comprising those compounds, and to the use of those compounds in the therapeutic treatment of the human or animal body and in the preparation of pharmaceutical compositions.

BACKGROUND TO THE INVENTION

The enzymes that are involved in the metabolism of polyamines, such as S-adenosyl-methionine decarboxylase (SAMDC) and ornithine decarboxylase (ODC), are the subject of intensive research. The background is that polyamines, such as spermine, spermidine and analogues thereof, play an important part in cell division and regulatory phenomena, for example in eukaryotic cells.

An early finding has been that higher levels of polyamines are to be found in cells that are dividing, for example in cancer cells, than in cells that are stable. Such observations have led to the conclusion that polyamines are necessary for cell proliferation.

The concept of influencing the polyamine level in cells has therefore been recognized and made use of in chemotherapy, for example of cancerous diseases.

Surprisingly, it has now been found that the compounds of the present invention exhibit especially valuable properties that can be used pharmacologically.

COMPLETE DESCRIPTION OF THE INVENTION

The compounds according to the invention are compounds of formula (I)

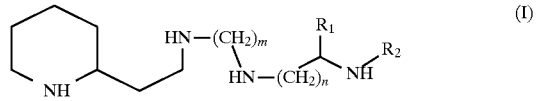

wherein either
  $R_1$ is hydrogen and
  $R_2$ is lower alkyl, lower alkenyl or lower alkynyl,
  m is 3 or 4 and
  n is 2 or 3;
or
  $R_1$ and $R_2$ together are tetramethylene,
  m is 3 or 4 and
  n is 2;
or salts thereof.

Within the context of the present Application, the general terms used hereinbefore and hereinafter have preferably the following meanings:

Lower alkyl has especially up to a maximum of 7 carbon atoms, is branched or unbranched and is preferably methyl or especially $C_2$–$C_7$alkyl, such as ethyl, n-propyl, isopropyl, n-butyl, isobutyl, sec-butyl, tert-butyl, n-pentyl, neopentyl, n-hexyl or n-heptyl, especially methyl or more especially $C_2$–$C_4$alkyl, such as ethyl, n-propyl, isopropyl, n-butyl, sec-butyl or isobutyl, special preference being given to ethyl and propyl, such as n-propyl.

Lower alkenyl has especially from 3 to 7, preferably 3 or 4, carbon atoms and has one or (less preferably) more double bonds. Preference is given, for example, to allyl or crotyl.

Lower alkynyl has especially from 3 to 7, preferably 3 or 4, carbon atoms and has one or (less preferably) more triple bonds. Preference is given, for example, to propyn-2-yl or 2-butyn-1-yl.

In lower alkenyl and lower alkynyl $R_2$, no unsaturated bonds originate from the carbon atom that is bonded to the nitrogen atom bonding $R_2$, since unstable compounds are otherwise formed.

Tetramethylene formed by $R_1$ and $R_2$ is —$(CH_2)_4$— and is bonded at both its terminal carbon atoms.

Salts are especially the pharmaceutically acceptable, that is to say non-toxic, salts of compounds of formula (I), that is to say especially the corresponding acid addition salts with acid anions that are not toxic (at the dose in question).

Such salts are formed, for example, by compounds of formula (I) with inorganic acids, for example hydrohalic acids, such as hydrochloric acid or hydrobromic acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also with amino acids, such as the 20 α-amino acids involved in the synthesis of proteins in nature, for example glutamic acid or aspartic acid, as well as with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acidic organic compounds, such as ascorbic acid. Carbonates or hydrogen carbonates are also possible.

Mixed salts include, for example, salts of compounds of formula (I) with di- or tri-valent acids that have acid radical with different dissociation constants, such as citric acid or phosphoric acid, where, for example, one or two protons of those acids have been replaced by cations, such as alkali metal cations, for example $Na^+$ or $K^+$, so that the corresponding salts still contain the corresponding cations as well as the compound of formula (I) and the corresponding acid anions.

For isolation or purification it is also possible to use pharmaceutically unacceptable salts, for example picrates or perchlorates. Only the pharmaceutically acceptable, non-toxic salts are used therapeutically, and those are therefore preferred.

The terms "compounds" and "salts" expressly include also individual compounds or individual salts.

Compounds of formula (I) can be in the form of pure isomers or in the form of mixtures of isomers, for example, provided that they contain a center of asymmetry, in the form of mixtures of enantiomers, such as racemic mixtures, or in the form of pure enantiomers; or, provided that they contain two or more centers of asymmetry, in the form of mixtures of diastereoisomers or in the form of pure diastereoisomers.

The compounds of the present invention exhibit especially valuable pharmacological properties. In particular, it has surprisingly been found that the compounds of formula (I) effect a reduction in the intracellular concentrations (pool) of natural polyamines, such as, especially, putrescine, spermidine and spermine. This brings about a slowing down or suppression of cell division, especially a reduction in or cessation of the growth of growing (especially rapidly growing) cells and tissues (growth is to be understood here as meaning cell division).

The reduction in the intracellular levels of polyamines, especially of putrescine, spermidine and/or spermine, presumably arises primarily from the fact that the compounds of formula (I) reduce the activities of biosynthetic enzymes of polyamine biosynthesis, ornithine decarboxylase (O)DC) and/or S-adenosylmethionine decarboxylase (SAMDC). Additionally or alternatively, the compounds of formula (I) can bring about an acceleration in the metabolic decomposition of natural polyamines; for example, induction of spermidine-spermine-acetyl-transferase, which in principle can even be super-induced, may be possible.

The reduction in the intracellular concentration of polyamines can be demonstrated, for example, as follows (see C. W. Porter et al., Cancer Res. 45, 2050–2057 (1985)):

Mouse ascites L1210 leukemia cells are cultured (at 37° C.) in RPMI-1640 medium (which comprises, per liter, 100 mg of $Ca(NO_3)_2$, 400 mg of KCl, 100 mg of $MgSO_4.7H_2O$, 6000 mg of NaCl, 2000 mg of $NaHCO_3$, 801 mg of $Na_2HPO_4$, 242 mg of L-Arg.HCl, 50 mg of L-Asn, 20 mg of L-Asp, 50 mg of L-Cys, 300 mg of L-Gln, 20 mg of L-Glu, 10 mg of Gly, 18.2 mg of $L-His.HCl.H_2O$, 20 mg of L-hydroxyproline, 50 mg of L-Leu, 40 mg of L-Lys.HCl, 15 mg of L-Met, 15 mg of L-Phe, 20 mg of L-Pro, 30 mg of L-Ser, 20 mg of L-Thr, 5 mg of L-Trp, 20 mg of L-Tyr, 20 mg of L-Val, 1 mg of 1-amino-benzoic acid, 0.2 mg of biotin, 3 mg of choline chloride, 1 mg of folic acid, 35 mg of i-inositol, 1 mg of nicotinamide, 0.25 mg of pantothenoic acid calcium salt, 1 mg of pyridoxine.HCl, 0.2 mg of riboflavin, 1 mg of thiamine.HCl, 0.005 mg of vitamin $B_{12}$, 2000 mg of glucose, 1 mg of glutathione, and 5 mg of phenol red), which also contains 2% 4-(2-hydroxyethyl)-1-piperazineethanesulfonic acid/3-(N-morpholino)propanesulfonic acid, 1 mM aminoguanidine and 10% NuSerum (Collaborative Research Inc., Lexington, Mass.). The cells are cultured under a humid 5% carbon dioxide atmosphere at 37° C. either in glass culture tubes (2 ml) or in 25 or 75 $cm^2$ tissue culture bottles in a total volume of 15 or 50 ml, respectively. The cultures are treated with the compounds of formula (I) or with 0.1 mM spermidine (controls: without the corresponding compounds) during the logarithmic growth phase (0.5 to $1\times10^5$ cells/ml). The number of cells is measured by electronic particle counting (Model ZF Coulter Counter; Coulter Electronics, Hialeah, Fla.) and confirmed from time to time by hemocytometer measurements. The viability of the cells is measured by trypan blue exclusion measurement (0.5% in unbuffered 0.9% sodium chloride solution).

For polyamine determination, the cell samples are washed twice in cold PBS (=phosphate-buffered saline—which comprises, per liter, 8000 mg of NaCl, 200 mg of KCl, 1150 mg of $Na_2HPO_4. 2H_2O$, 200 mg of $KH_2PO_4$, 100 mg of $MgCl_2.H_2O$, 200 mg of $MgSO_4.H_2O$ and $CaCl_2$; pH 7.2), and an aliquot of $10^7$ cells is removed for polyamine determination. The cells are pelletized, and the PBS supernatant is removed carefully using a cotton wool swab. The pellet containing the cells is then maintained at 4° C. for 30 minutes, together with 0.5 ml of 0.6M perchloric acid, and is then centrifuged at 12 000 g for 3 minutes using a microcentrifuge. The supernatant is frozen at −20° C. until the HPLC analysis. For that purpose, the polyamines in a 50 μl sample of the perchloric acid extract are separated over an HPLC system using a glass "Microbore Column" having a diameter of 2.8 mm, which is packed to a height of 2 cm with TLC-4A-cation exchange resin (Durrum Chemical Corp., Palo Alto, Calif.). The column temperature is maintained at 65° C. by means of a water bath with circulating water. The column is eluted at a flow rate of 16 ml/hour with an initial column pressure of 34.45 bar, which decreases as the ionic strength of the elution buffer increases. Buffer 1 (which comprises 0.2M boric acid, 0.5M NaCl, 0.03% Brij 35 (polyoxyethylene monolauryl ether, the number of ethyleneoxy radicals is approximately 23; Pierce Chemical Co., Rockford, Ill.) and 0.0001% octanoic acid, pH adjusted to 6.0 with saturated KOH) is flushed through the column for 4 minutes. Buffer 2 (which comprises 0.2M boric acid, 2.15M NaC, 0.03% Brij 35 and 0.0001% octanoic acid, pH adjusted as above) is pumped through for 6 minutes. Buffer 3 (which comprises 0.2M boric acid, 2.9M NaCl and 0.0001% octanoic acid (pH adjusted as above)) is likewise applied for 6 minutes. The column is re-equilibrated with buffer 1 for 10 minutes, before the next sample is introduced. The column eluate is derivatized with 0.05% o-phthalaldehyde (Durrum Chemical Corp.) in 0.4M borate buffer (pH 10.4)/1 mM 2-mercaptoethanol/0.09% Brij 35. The flow rate for o-phthalaldehyde is 8 ml/hour. The derivatized eluate is examined for its polyamine content by being passed through the flow cell of a flow-measuring device (Fluoro-Monitor; American Instrument Co., Silver Spring, Md.) with a fixed excitation wavelength of 360 nm and an emission wavelength of 570 nm. The data are determined using a Hewlett-Packard Model 3385A automation system. The variance of the system for a standard with known concentrations of putrescine, spermidine and spermine hydrochloride is lower than 5%. The sensitivity of the HPLC system is approximately 50 pmol/50 μl sample ($10^6$ cells).

Using this method it is possible to observe a reduction in the polyamine levels with the compounds of formula (I) of the present invention. In particular, at a concentration of a compound of formula (I) of from 10 to 50 μM, the average levels of putrescine, spermidine and spermine are each reduced to less than 50% of the control values, especially, at 10 μM, to 10 to 40% in the case of putrescine, 5 to 20% in the case of spermidine and 5 to 30% in the case of spermine.

As polyamine antimetabolites, the compounds of formula (I) have antiproliferative properties which can be demonstrated, for example, by identifying the inhibitory action on the growth of human T24 bladder cell carcinomas. This is demonstrated by incubating the cells in Eagle's minimal essential medium (see Eagle, H., Science 130, c1432–1437 (1959)), to which 5% (v/v) fetal calf serum is added, in a humidified incubator at 37° C. and 5% by volume $CO_2$ in the air. The carcinoma cells (1000–1500) are transferred to 96-well microtiter plates and are incubated overnight under the conditions indicated. The test compound is added in serial dilutions on day 1. The plates are incubated for 5 days under the conditions indicated. During that period, control cultures undergo at least 4 cell divisions. After incubation. the cells are fixed with 3.3% (weight/volume=w/v) aqueous glutaraldehyde solution, washed with water and stained with 0.05% (w/v) aqueous methylene blue solution. After washing, the dye is eluted with 3% (w/v)

aqueous hydrochloric acid. The optical density (OD) per well, which is directly proportional to the number of cells, is then measured by means of a photometer (Titertek multiskan) at 665 nm. The $IC_{50}$ values are calculated by means of a computer system using the formula $$\frac{OD_{665}(\text{test}) - OD_{665}(\text{start})}{OD_{665}(\text{control}) - OD_{665}(\text{start})} \times 100$$

The $IC_{50}$ value is defined as the concentration of active ingredient at which the number of cells per well at the end of the incubation period is only 50% of the number of cells in the control cultures.

For compounds of formula (I), $IC_{50}$ values in the range of from $10^{-5}$ to $5\times10^{-8}$M, especially in the range of from $2\times10^{-6}$ to $10^{-7}$M, are obtained.

Since a reduction in the polyamine concentration brings about an inhibition of cell growth, it is possible by administering compounds of formula (I) to inhibit the growth of both eukaryotic and prokaryotic cells and even to kill cells or inhibit the onset of cell differentiation. For example, tumors, for example tumors produced in models by, for example, the syngeneic transplantation of tumor cells, can be controlled. Syngeneic transplantation means transplantation within a strain of genetically virtually identical individuals.

Using test systems that are known per se (see, for example, Brun, R., and Kunz, C., Acta Tropica 46, 361–368 (1989)), it is also possible to demonstrate the effectiveness of the compounds of formula (I) against trypanosomes.

The compounds of formula (I) are therefore especially suitable for the (therapeutic or prophylactic) treatment of pathological conditions that are responsive to a reduction in the concentration of polyamines in cells (intracellular polyamine concentration), for example proliferative diseases, especially benign and malignant tumor diseases. They can bring about the regression of tumors and also prevent the spread of tumor cells (metastasisation) and the growth of micrometastases. Moreover, they can be used, for example, for treating protozoal infections, for example trypanosomiasis, malaria, or opportunistic infections, such as pulmonary inflammation caused by *Pneumocystis carinii*.

The corresponding diseases can be treated in warm-blooded animals, especially in mammalian domestic animals and in humans.

The compounds of formula (I) can be used as polyamine antimetabolites either on their own or in combination with other substances having pharmacological activity. They can be combined with, for example, (a) inhibitors of one or more enzymes of polyamine biosynthesis, for example ornithine decarboxylase inhibitors or S-adenosylmethionine decarboxylase inhibitors, (b) inhibitors of protein kinase C, (c) inhibitors of tyrosine protein kinase(s), (d) cytokines, (e) negative growth regulators, (f) aromatase inhibitors, (g) antioestrogens or (h) conventional cytostatic active ingredients.

Preference is given to compounds of formula (I) wherein either $R_1$ is hydrogen and $R_2$ is lower alkyl or lower alkenyl, m is 3 or 4 and n is 2 or 3;

or $R_1$ and $R_2$ together are tetramethylene, m is 3 or 4 and n is 2;

or salts thereof.

Special preference is given to compounds of formula (I) wherein either $R_1$ is hydrogen and $R_2$ is lower alkyl, especially ethyl or n-propyl, or lower alkenyl, especially allyl;

or $R_1$ and $R_2$ together are tetramethylene;

m is 3 and n is 2;

or salts thereof.

Very special preference is given to compounds of formula (I) wherein $R_1$ is hydrogen and $R_2$ is lower alkyl, especially ethyl or propyl, m is 3 and n is 2;

or salts thereof.

Very special preference is given also to a compound of formula (I) wherein $R_1$ and $R_2$ together are tetramethylene, m is 3 and n is 2;

or a salt thereof.

The compounds of formula (I) mentioned in the Examples, or their pharmaceutically acceptable salts, are very especially preferred.

The compounds of formula (I) according to the invention are prepared by processes known per se, for example a) for the preparation of compounds of formula (I) wherein $R_1$ is hydrogen and $R_2$ is lower alkyl, or $R_1$ and $R_2$ together are tetramethylene, by reducing a pyridyl compound of formula (II)

wherein $R_3$ is 2-(2-piperidyl)-ethyl or 2-(2-pyridyl)-ethyl and either m is 3 or 4, n is 2 or 3 and $R_4$ is a radical of formula (A.)

wherein $R_1'$ is hydrogen and $R_2'$ is lower alkyl, lower alkenyl or lower alkynyl;

or m is 3 or 4, n is 2 and $R_4$ is 2-piperidyl or 2-pyridyl, wherein in the compound of formula (II)

(i) at least one of the two radicals $R_3$ and $R_4$ contains a 2-pyridyl radical, and (ii) the nitrogen atoms can be free or completely or partially in protected form, to form a piperidyl compound, and removing any protecting groups that are present; or b) for the preparation of compounds of formula (I) wherein $R_1$ is hydrogen, $R_2$ is lower alkyl, lower alkenyl or lower alkynyl, m is 3 or 4 and n is 2 or 3, by reacting a piperidyl compound of formula (III)

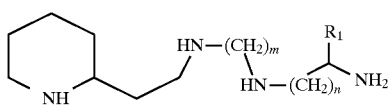

(III)

wherein
R₁ is hydrogen and
n and m are as defined for compounds of formula (I), with a compound of formula (IV)

$$R_2'-X \quad (IV)$$

wherein
R₂' is lower alkyl, lower alkenyl or lower alkynyl and
X is a nucleofugal leaving group;
primary and secondary amino groups in the compound of formula (III) each being in monoprotected form;
and removing any protecting groups that are present; or
c) by reacting a piperidyl compound of formula (V)

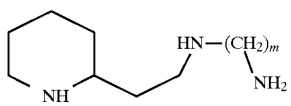

(V)

wherein
m is 3 or 4, with a compound of formula (VI)

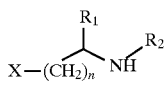

(VI)

wherein
R₁, R₂ and n are as defined for compounds of formula (I) and X is a nucleofugal leaving group;
primary and secondary amino groups in the compounds of formula (V) and formula (VI) each being in monoprotected form;
and removing any protecting groups that are present; or
d) by reacting a piperidyl compound of formula (VII)

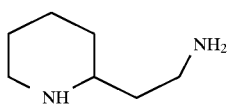

(VII)

with a compound of formula (VIII)

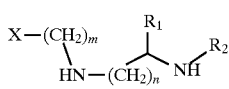

(VIII)

wherein
R₁, R₂, m and n are as defined for compounds of formula (1); and X is a nucleofugal leaving group
primary and secondary amino groups in the compounds of formula (VII) and formula (VIII) each being in mono-protected form;
and removing any protecting groups that are present;
it being possible for the starting materials in processes a) to d) to be in the form of their salts, provided that salt-forming groups are present;
and, if desired, converting an obtainable salt of a compound of formula (I) into the free compound or into a different salt of a compound of formula (I), converting an obtainable free compound of formula (I) into its salt, and/or separating obtainable mixtures of isomers into isomers.

DETAILED DESCRIPTION OF THE PROCESS CONDITIONS

In the process descriptions hereinbefore and hereinafter, R₁, R₂, n and m are as defined for compounds of formula (I), unless indicated otherwise.

Process a) (reduction)

Reduction is suitable especially for the preparation of compounds of formula (I) wherein R₁ is hydrogen and R₂ is lower alkyl or R₁ and R₂ together are tetramethylene, since lower alkenyl or lower alkynyl R₂ is generally reduced more readily than is a pyridyl that in every case has to be hydrogenated.

Reduction is preferably carried out by catalytic hydrogenation, or by reaction with an alkali metal in an alcohol.

In the case of catalytic hydrogenation, the reaction with hydrogen is carried out under preferred pressures of from 0.01 to 20 MPa (which corresponds approximately to 0.1 to 200 atm), especially from approximately 0.1 to 1 MPa (1 to 10 atm), in the presence of heavy metal or heavy metal oxide catalysts, such as noble metals or noble metal oxides, for example platinum, platinum oxide, palladium, palladium oxide, rhodium or rhodium oxide or mixtures thereof, or nickel, such as especially a platinum dioxide catalyst according to Adams and/or a rhodium oxide/platinum oxide (=Rh(III)/Pt(VI) oxide) catalyst according to Nishimura (see S. Nishimura, Bull. Chem. Soc. Japan 33, 566 (1960)), each of which can be in free form (nickel, for example, in the form of a skeleton catalyst=Raney nickel), in the form of an alloy (for example Ni/Al alloy) or bonded to a carrier, such as activated carbon, barium or strontium sulfate, calcium carbonate or aluminum oxide, preferably in free form. There are used as solvents especially alcohols, such as lower alkanols, for example methanol or ethanol, also water, lower alkyl esters of lower alkanoic acids, such as ethyl acetate, ethers, for example cyclic ethers, such as dioxane, oxo-lower alkanes, such as acetaldehyde or acetone, lower alkanoic acids, such as glacial acetic acid, and mixtures of those solvents. While hydrogenation with noble metals or their oxides is preferably carried out in a neutral or acid medium (for example in glacial acetic acid or with the addition of mineral acids), a neutral or alkaline medium is preferred when nickel is u:ed. Temperatures are preferably from 0° C. to the reflux temperature of the reaction mixture in question, especially from approximately 18° C. to approximately 65° C.

Reaction with an alkali metal, such as potassium or especially sodium, in an alcohol, such as especially a lower alkanol, for example ethanol or butanol, is carried out under customary conditions, for example at temperatures of from 0° C. to approximately 50° C.

In the starting materials of formula (II), all the amino groups, other than those which are ring atoms of pyridyl radicals, are preferably in unprotected form or, especially, in mono-protected form; in the latter case, the two or three secondary amino groups in the starting material of formula (II) each have a bond to a protecting group instead of the bond to a hydrogen atom. It is, however, also possible for only some of the secondary amino groups to be in protected form.

The protecting groups for amino groups in starting materials, the reaction of which is to be avoided, include especially those protecting groups (conventional protecting groups) that are conventionally employed in the synthesis of peptide compounds and also of cephalosporins and penicillins as well as nucleic acid derivatives. Those protecting groups may already be present in the precursors and are intended to protect the functional groups in question from undesired secondary reactions, such as acylation, esterification, oxidation, solvolysis, etc. A characteristic of protecting groups is that they are readily removable, that is to say without undesired secondary reactions taking place, for example by solvolysis, by reduction (without the simultaneous reduction of double bonds or of any triple bonds that may be present), by photolysis or enzymatically, for example also under physiological conditions. A characteristic of protecting groups is that they are not present in the end products.

The protection of functional groups by such protecting groups, the protecting groups themselves and the reactions for their removal are described, for example, in standard works, such as J. F. W. McOmie, "Protective Groups in Organic Chemistry", Plenum Press, London and New York 1973, in Th. W. Greene and P. G. M. Wuts, "Protective Groups in Organic Synthesis", second edition, Wiley, New York 1991, in "The Peptides"; Vol. 3 (E. Gross and J. Meienhofer, eds.), Academic Press, London and New York 1981, in "Methoden der organischen Chemie", Houben-Weyl, 4th edition, Vol. 15/I, Georg Thieme Verlag, Stuttgart 1974, and in H. -D. Jakubke and H. Jescheit, "Aminos äuren, Peptide, Proteine", Verlag Chemie, Weinheim, Deerfield Beach and Basle 1982.

A protected amino group i s protected by a monovalent amino-protecting group, for example in the form of an acylamino, arylmethylamino, 2-acyl-lower alk-1-enylamino or silylamino group. Divalent protecting groups bridging two adjacent nitrogen atoms are also possible. The term "monoprotected" in connection with protected amino groups means that each protected amino group has a bond to the protecting group—nevertheless, divalent protecting groups can also be present, which then bond to two different amino groups.

Hereinafter an "amino" -protecting group is always to be understood as meaning also a corresponding imino-protecting group (protecting group for an unprotected secondary amino group).

In an acylamino group acyl is, for example, the acyl radical of an organic carboxylic acid having, for example, up to 18 carbon atoms, especially of a lower alkanecarboxylic acid that is unsubstituted or substituted, for example, by halogen or by aryl, or of a benzoic acid that is unsubstituted or substituted, for example, by halogen, lower alkoxy or by nitro, or preferably of a carbonic acid semiester. Such acyl groups are preferably lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloroacetyl, benzoyl that is unsubstituted or substituted, for example, by halogen, lower alkoxy or by nitro, such as benzoyl, 4-chlorobenzoyl, 4-methoxybenzoyl or 4-nitrobenzoyl, lower alkoxycarbonyl, preferably lower alkoxycarbonyl that is branched at the 1-position of the lower alkyl radical or that is suitably substituted at the 1- or 2-position, for example tert-lower alkoxycarbonyl, such as tert-butoxycarbonyl, arylmethoxycarbonyl having one, two or three aryl radicals which are phenyl that is unsubstituted or mono- or polysubstituted, for example, by lower alkyl, especially tert-lower alkyl, such as tert-butyl, lower alkoxy, such as methoxy, hydroxy, halgen, such as chlorine, and/or by nitro, for example benzyloxycarbonyl 4-nitrobenzyloxycarbonyl, diphenylmethoxycarbonyl, 9-fluorenylmethoxycarbonyl or di(4-methoxyphenyl)methoxycarbonyl, aroylmethoxycarbonyl wherein the aroyl group is preferably benzoyl that is unsubstituted or substituted by, for example, halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(triarylsilyl-lower alkoxycarbonyl, for example 2-trilower alkylsilyl-lower alkoxycarbonyl, such as 2-trimethylsilylethoxycarbonyl or 2-(di-n-butylmethylsilyl) ethoxycarbonyl, or triarylsilyl-lower alkoxycarbonyl, for example 2-triphenylsilylethoxycarbonyl. Especially important amino- (and imino-acyl-) protecting groups are suitable organic sulfonic acid radicals, such as arylsulfonic acid radicals, especially phenylsulfonyl radicals or mono-, di- or tri-lower alkylphenylsulfonyl radicals, such as benzene-, toluene- or mesitylene-sulfonyl, or aryl-lower alkylsulfonyl radicals, especially phenyl-, mono-lower alkylphenyl-, di-lower alkylphenyl- or tri-lower alkylphenyl-lower alkylsulfonyl, such as benzyl-, mesitylene- or 4-methylbenzylsulfonyl; and/or suitable organic phosphoryl radical, such as diarylphosphinyl, especially diphenylphosphinyl ([Phe]$_2$ (P=O)—, or, most especially, di(lower alkoxy)phosphoryl, such as diethoxyphosphoryl ([H$_3$C-CH$_2$O—]$_2$—(P=O)—).

In an arylmethylamino group, for example a mono-, di- or, especially, tri-arylmethylamino group, the aryl radicals are especially unsubstituted or substituted phenyl radicals. Such groups are, for example, benzyl-, diphenylmethyl- or, especially, trityl-amino.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk- 1-en-2-yl, for example lower alkoxycarbonyl-prop- 1 -en-2-yl, such as 1-ethoxycarbonyl-prop-1-en-2-yl.

A silylamino group is, for example, a tri-lower alkylsilylamino group, for example trimethylsilylamino or tert-butyldimethylsilylamino. It is also possible for the silicon atom of the silylamino group to be substituted by only two lower alkyl groups, for example methyl groups, and by the amino group or carboxy group of a second molecule of formula (I). Compounds having such protecting groups can be prepared, for example, using the corresponding chlorosilanes, such as dimethylchlorosilane, as silylating agent.

Two divalent amino-protecting groups (preferably bridging adjacent nitrogen atoms) are also possible, such as unsubstituted or mono- or di-substituted methylene groups, such as 1-lower alkoxy (for example methoxy or ethoxy)-lower alkylene (for example ethylene or 1-n-butylene), for example —C(CH$_3$)(OC$_2$H$_5$)—, especially mono- or di-lower alkyl- or phenyl-methylene, for example —C(CH$_3$)$_2$— or —CH(-phenyl)-; methylene (—CH$_2$—) is especially preferred.

Preferred amino-protecting groups are lower alkoxycarbonyl, phenyl-lower alkoxycarbonyl, fluorenyl-lower alkoxycarbonyl, mono-, di- or tri-lower alkylphenylsulfonyl, di(lower alkoxy)phosphoryl, 2-lower alkanoyl-lower alk-1-en-2-yl or lower alkoxycarbonyl-lower alk-1-en-2-yl, with special preference being given to tert-butoxycarbonyl, mesitylenesulfonyl, toluenesulfonyl and/or diethoxyphosphoryl, especially tert-butoxycarbonyl.

The following reaction conditions are preferably to be employed for the removal of protecting groups:

A protected amino group is freed in a manner known per se and, depending upon the nature of the protecting groups, by different methods, preferably by means of solvolysis or selective reduction, for example in the manner described in the standard works mentioned at the beginning. Lower alkoxycarbonylamino, such as tert-butoxycarbonylamino, arylmethoxycarbonylamino, such as (unsubstituted or substituted) benzyloxycarbonylamino, or di(lower alkoxy) phosphoryl can be removed in the presence of acids, for example mineral acids, e.g. a hydrogen halide, such as hydrogen chloride or hydrogen bromide, or sulfuric or phosphoric acid, preferably in the presence of hydrogen chloride, in polar solvents, such as water, alcohols, such as lower alkanols, e.g. methanol or ethanol, a carboxylic acid, such as acetic acid, or ethers, preferably cyclic ethers, such as tetrahydrofuran or dioxane (preferred in the case of the removal of di-lower alkoxyphosphoryl), or mixtures of two or more of the mentioned solvents, especially in aqueous-alcoholic solutions, such as water/methanol mixtures; and 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be removed, for example, by treatment with a suitable reducing agent such as zinc in the presence of a suitable carboxylic acid, such as aqueous acetic acid. Aroylmethoxycarbonylamino can also be removed by treatment with a nucleophilic, preferably salt-forming reagent, such as sodium thiophenolate, and 4-nitrobenzyloxycarbonylamino can also be removed by treatment with an alkali metal dithionite, for example sodium dithionite. Unsubstituted or substituted diphenylmethoxycarbonylamino, tert-lower alkoxycarbonylamino or 2-(trisubstituted silyl)-lower alkoxycarbonylamino, such as 2-tri-lower alkylsilyl-lower alkoxycarbonylamino, can be removed by treatment with a suitable acid, for example formic acid or trifluoroacetic acid, and unsubstituted or substituted triarylmethylamino or formylamino can be removed, for example, by treatment with an acid, such as a mineral acid, for example hydrochloric acid, or an organic acid, for example formic acid, acetic acid or trifluoroacetic acid, in the absence or presence of water, and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and subsequent solvolysis, such as alcoholysis or hydrolysis, of the resulting substitution product. An amino group protected by 2-(trisubstituted silyl)-lower alkoxycarbonyl, such as 2-tri-lower alkylsilyl-lower alkoxycarbonyl, can also be converted into free amino (or imino) by treatment with a salt of hydrofluoric acid that yields fluoride anions, such as an alkali metal fluoride, for example sodium or potassium fluoride, in the absence or presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Silyl, such as trimethyisilyl, bonded directly to a hetero atom, such as nitrogen, can likewise be removed by means of fluoride ions. An amino group protected by diarylphosphinyl, such as diphenylphosphinyl, can be freed in the presence of a Lewis acid, especially boron trifluoride etherate, such as boron trifluoride ethyl etherate or methyl etherate, in suitable solvents or solvent mixtures, for example alcohols, such as methanol or ethanol, halogenated hydrocarbons, such as chloroform or methylene chloride, ethers, such as dimethyl or diethyl ether, or especially mixtures thereof, such as methanol/-methylene chloride/dimethyl or diethyl ether, at preferred temperatures of from −10° C. to the respective reflux temperature, especially from 0° C. to room temperature, preferably under a protecting gas, such as $N_2$.

An amino group protected in the form of a sulfonamide is preferably freed by acid hydrolysis, for example in the presence of a mineral acid, such as especially a hydrohalic acid, such as hydrobromic acid, in an alcohol, especially an aryl alcohol, such as phenol, in the presence or absence of a carboxylic acid, such as a lower alkanoic acid, for example acetic acid, at preferred temperatures of from 60° C. to reflux temperature, or by acid hydrolysis with concentrated sulfuric acid.

An amino group protected by di(lower alkoxy)phosphoryl is preferably freed by acid hydrolysis, for example in the presence of a hydrogen halide, such as hydrogen bromide or especially hydrogen chloride (which is preferably introduced in gaseous form), in an ether, especially a cyclic ether, such as tetrahydrofuran, at preferred temperatures of from −10° C. to the reflux temperature of the reaction mixture in question, for example at from approximately 0° C. to approximately room temperature.

Nitrogen atoms protected by a divalent protecting group bridging two adjacent nitrogen atoms are preferably freed by acidolytic cleavage, for example with mineral acids, such as hydrohalic acids, for example hydrochloric or hydrobromic acid, or under milder conditions similar to Knoevenagel conditions, for example with malonic acid or cyanoacetic acid in the presence of a tertiary nitrogen base, such as pyridine (see, for example, Nagarajan et al., J. Org. Chem. 50, 5735–5737 (1985)).

The temperatures at which the protected functional groups are freed are preferably from −80° C. to reflux temperature, especially from−20° C. to 50° C. or from 80° C. to 110° C., for example from 0° C. to 35° C., such as in the range of from 0° C. to room temperature, or approximately at reflux temperature.

In the following description of the preparation of starting materials, protecting groups, where required, are introduced at suitable stages (see hereinafter under "General process conditions"), the protecting groups preferably being selected from those mentioned above and being removed at suitable stages as described there.

Starting materials of formula (II) can be prepared by processes known per se. For example, they can be obtained by reacting a compound of formula (IX)

wherein $R_3$ is 2-(2-pyridyl)-ethyl or 2-(2-piperidyl)-ethyl and m is 3 or 4, with a compound of formula (X)

wherein $R_4$ and n are as defined for compounds of formula (II) and X is a nucleofugal leaving group, in the manner defined in greater detail below under process b) for compounds of formula (IV), the secondary amino groups in the compound of formula (IX) and the compound of formula (X)—and, if desired, also the primary amino group in the compound of formula (IX)—each being in monoprotected form, with the proviso that at least one of the radicals $R_3$ and $R_4$ contains a 2-pyridyl radical.

The reaction is carried out exactly analogously to the preferred conditions described below (process b)) for the reaction of compounds of formula (III) with compounds of formula (IV), the compound of formula (IX) being used instead of the compound of formula (III) and the compound of formula (X) being used instead of the compound of formula (IV).

An unprotected precursor of a compound of formula (II), wherein m is 3 or 4, n is 2, $R_3$ is 2-(2-pyridyl)-ethyl or 2-(2-piperidyl)-ethyl and $R_4$ is 2-pyridyl, is also prepared from a diamine of formula (XI)

$$H_2N-(CH_2)_m-NH_2 \qquad (XI),$$

wherein m is 3 or 4, which is, for example, available commercially (e.g. Aldrich, Buchs, Switzerland), by reaction with commercially available 2-vinylpyridine (e.g. Fluka, Buchs, Switzerland), for example by simple heating in solvents, especially water, at preferred temperatures of from 50° C. to reflux temperature, for example at approximately 100° C.

When a suitable ratio of the molar amounts is employed, for example when the 2-vinylpyridine is used in a slightly greater molar amount relative to the molar amount of the compound of formula (XI), for example in an amount that is approximately from 1.05 to 5 times, especially from approximately 1.5 to approximately 2.5 times, the molar amount, the last-mentioned reaction additionally yields also the unprotected precursor of a compound of formula (IX), wherein $R_3$ is 2-(2-pyridyl)-ethyl and the other radicals and symbols are as defined for compounds of formula (IX). Hydrogenation analogously to the conditions for the hydrogenation of compounds of formula (II) yields the corresponding unprotected precursor of the compound of formula (IX), wherein $R_3$ is 2-(2-piperidyl)-ethyl. The correspondingprotected or partially protected compounds of formula (IX) can be obtained from the unprotected precursors—the introduction of the protecting groups is preferably carried out in the manner described hereinafter under "General process conditions", there being suitable as protecting groups principally those mentioned above for compounds of formula (II), especially tert-butoxycarbonyl.

A compound of formula (X) can be prepared, for example, by reacting the corresponding hydroxy precursor of formula (XII)

$$R_4-(CH_2)_n-OH \qquad (XII),$$

wherein $R_4$ and n are as defined for compounds of formula (X) and secondary amino groups are in protected form, under mild conditions, with an activated derivative of an acid H—X, wherein X is as defined for compounds of formula (X) (except when H—X is hydrazoic acid or a hydrohalic acid), for example an acid chloride or acid bromide of the formula Cl—X or Br—X, if necessary in the presence of a tertiary nitrogen base, such as triethylamine, in order to avoid the removal of acid-labile protecting groups or, when X is a halogen, such as chlorine, bromine or iodine, under mild conditions by reaction with the corresponding halosuccinimide, such as bromosuccinimide, in the presence of a triarylphosphine, especially triphenylphosphine, in suitable solvents, such as chlorinated hydrocarbons, for example chloroform or dichloromethane, at preferred temperatures of from −20° C. to 50° C., especially from approximately 0° C. to approximately 20° C. A compound of formula (X) wherein X is hydroxy esterified by hydrazoic acid is then obtained, for example, by nucleophilic substitution of a compound of formula (X) wherein the radical X is bromine or iodine, under customary conditions.

Compounds of formula (XII) are known, can be prepared by processes known per se or are available commercially, for example 2-(2-hydroxyethyl)-pyridine and 2-(2-hydroxyethyl)-piperidine are available commercially (Aldrich, Buchs, Switzerland), while corresponding N-lower alkyl-, N-lower alkenyl- or N-lower alkynyl-amino-$(CH_2)_n$ alcohols are likewise known, are available commercially or can be prepared by processes known per se. Where secondary nitrogen atoms that have to be protected are present, the corresponding protected (compounds of formula (X) are obtained therefrom by introducing protecting groups analogously to the conditions mentioned hereinafter under "General process conditions".

A compound of formula (II) wherein either m is 3 and n is 2 or m is 4 and n is 3, $R_3$ is 2-(2-pyridyl)-ethyl and $R_4$ is a radical of formula (A) as defined under formula (II) is also prepared from a triamine of formula (XIII)

$$H_2N-(CH_2)_m-NH-(CH_2)_n-CHR_1'-NH_2 \qquad (XIII),$$

wherein m is 3 or 4 and n is 2 or 3 (preferably, either m is 3 and n is 2, or m is 4 and n is 3) and $R_1'$ is hydrogen, and which is known, can be prepared by processes known per se or is available, for example, commercially (for example, bis(3-aminopropyl)amine from Fluka, Buchs, Switzerland), by reaction with commercially available 2-vinylpyridine (e.g. Fluka, Buchs, Switzerland), for example by simple heating in solvents, especially water, lower alkanoic acids, such as acetic acid, or mixtures thereof, at preferred temperatures of from 50° C. to reflux temperature, for example at approximately from 90° C. to 110° C.

When a suitable ratio of the molar amounts is employed, for example when the 2-vinylpyridine is used in an approximately equal to slightly greater molar amount relative to the molar amount of the compound of formula (XIII), for example in an amount that is approximately from 0.95 to 1.4 times, especially from approximately 1.0 to approximately 1.2 times, the molar amount, the last-mentioned reaction yields a compound of formula (XIV)

$$R_3-NH-(CH_2)_m-NH-(CH_2)_n-CHR_1'-NH_2 \qquad (XIV)$$

wherein $R_3$ is 2-(2-pyridyl)-ethyl and the other radicals are as defined for compounds of formula (XIII).

For the preparation of asymmetric compounds of formula (XIV) (m is 3, n is 3; or m is 4, n is 2), it is possible, if necessary, to protect one of the primary amino groups in order thus to obtain better yields.

The corresponding protected compounds of formula (XIV) (which carry at each primary and secondary nitrogen atom a single-bonded protecting group) can be prepared from the unprotected or only partially protected precursors—the introduction of the protecting groups is preferably carried out in the manner described hereinafter under "General process conditions", there being used as protecting groups principally those mentioned above for compounds of formula (II), especially tert-butoxycarbonyl.

Subsequent reaction of a protected compound of formula (XIV) with a compound of formula (IV) as defined under process b), under conditions analogous to those mentioned therein, yields the corresponding compounds of formula (II). The reaction of compounds of formula (XIII) via compounds of formula (XIV) to form the corresponding (protected) compounds of formula (II) can also be carried out without isolating the intermediates.

Process b) (nucleophilic substitution)

In the piperidyl compound of formula (III), the nitrogen atoms are each in monoprotected form (one bond to a protecting group per nitrogen atom). There come into consideration as protecting groups especially the amino-protecting groups mentioned under process a). The protecting groups are preferably introduced in the manner described hereinafter under "General process conditions".

The following proviso applies (because of the above definition of the resulting radical $R_2$ for compounds of formula (I)): in the compound of formula (IV), no unsaturated bond in lower alkenyl or lower alkynyl $R_2'$ originates from the carbon atom that is bonded to the nucleofugal leaving group X.

A nucleofugal leaving group X in a compound of formula (IV) is especially a leaving group selected from hydroxy esterified by a strong inorganic or organic acid, especially hydroxy esterified by a mineral acid, for example a hydrohalic acid, such as hydrochloric, hydrobromic or hydriodic acid, or by a strong organic sulfonic acid, such as a lower alkanesulfonic acid that is unsubstituted or substituted, for example, by halogen, such as fluorine, or an aromatic sulfonic acid, for example a benzenesulfonic acid that is unsubstituted or substituted by lower alkyl, such as methyl, halogen, such as bromine, and/or by nitro, such as a methanesulfonic acid, p-bromobenzenesulfonic acid or p-toluenesulfonic acid, or hydroxy esterified by hydrazoic acid. The compound in question can also be prepared in situ by replacing a radical X, for example Cl, by a different radical X, for example I (preferably by an alkali metal iodide, such as NaI), and then reacting it further in the resulting reaction mixture.

In a starting material of formula (IV), X is preferably halogen, such as chlorine, bromine or iodine, especially bromine or iodine.

The reaction is preferably carried out in the presence of a strong base, such as an alkali metal hydride, for example sodium hydride or potassium hydride, or an alkali metal amide, such as sodium amide, or an alkali metal di-lower alkylamide, such as lithium diisopropylamide, especially in the presence of sodium hydride or potassium hydride, which can be added, for example, in the form of a dispersion in oil or after extraction of the oil, for example with a liquid hydrocarbon, such as hexane, using an equimolar amount, relative to the molar amount of the compound of formula (III), or preferably an excess of the base, for example an amount that is from 1 to 20 times, especially from 2 to 10 times, the molar amount, at preferred temperatures of from −10° C. to the reflux temperature of the reaction mixture, especially at from approximately 5° C. to approximately 60° C., or (where starting materials having phosphoryl-protected amino groups are used) at from 10° C. to reflux temperature, for example at from 20° C. to 80° C., in aprotic, especially polar, solvents, such as acid amides, for example dimethylformamide, diethylformamide, 1,3-dimethyl-3,4,5,6-tetrahydro-2(1H)-pyrimidinone (DMPU) or hexamethylphosphoric acid triamide, aromatic hydrocarbons, such as toluene or benzene (in which case preferably in the presence of a phase-transfer catalyst, for example a tetra-lower alkylammonium halide, such as tetra(n-butyl)ammonium bromide), ethers, for example cyclic ethers, such as dioxane, or mixtures of such solvents, in the presence or absence of a protecting gas, such as argon or nitrogen; it being possible to remove the ammonia that is formed when alkali metal amides are used as bases by, for example, application of a vacuum, for example of from 0.1 to 100, especially from 0.5 to 10, torr.

The compound of formula (IV) is preferably used in an equimolar amount or in excess relative to the compound of formula (III), especially in an amount that is from 1 to 20 times, especially from 2 to 10 times, the molar amount, relative to the compound of formula (III).

When the protecting group at the nitrogen atom to be alkylated by $R_2'$ is an organic sulfonic acid radical, such as arylsulfonyl, especially phenylsulfonyl or lower alkylphenyl-sulfonyl, such as benzene- or toluene-sulfonyl, or aryl-lower alkylsulfonyl, especially phenyl- or lower alkylphenyl-lower alkylsulfonyl, such as benzyl- or 4-methylbenzyl-sulfonyl, the alkylation with a compound of formula (IV) can preferably be carried out in the presence of weaker bases, such as especially metal hydroxides or carbonates, such as especially alkali metal hydroxides, for example sodium or potassium hydroxide, or alkaline earth metal carbonates or alkali metal carbonates, for example sodium or potassium carbonate, preferably in the last-mentioned solvents, especially in halogenated hydrocarbons, such as dichloromethane or chloroform, and more especially in carboxylic acid amides, such as dimethylformamide or dimethylacetamide, and at the temperatures indicated and preferably under a protecting gas, such as nitrogen or argon.

The removal of the protecting groups, especially of the tert-butoxycarbonyl protecting group, from the resulting protected compounds of formula (I) is preferably carried out under the conditions described under process a).

Starting materials of formula (III) can be obtained by hydrogenation analogously to the conditions for the hydrogeration of compounds of formula (II) from compounds of formula (XIV), as defined above, the corresponding (unprotected) compounds of formula (III) being obtained. The corresponding protected compounds of formula (XIV) (which carry at each primary and secondary nitrogen atom a single-bonded protecting group) can be obtained from the unprotected or only partially protected precursors—the introduction of the protecting groups is preferably carried out in the manner described hereinafter under "General process conditions", there being suitable as protecting groups principally those mentioned above for compounds of formula (II), especially tert-butoxycarbonyl.

Compounds of formula (IV) are known, can be prepared by processes known per se or are available commercially.

Of course, the proviso of process a) that at least one 2-pyridyl radical must be present does not apply in respect of the compound of formula (III) and the starting materials.

Process c) (nucleophilic substitution)

In the piperidyl compound of formula (V) and the compound of formula (VI), the nitrogen atoms are each in monoprotected form (one bond to a protecting group per nitrogen atom). There come into consideration as protecting groups especially the amino-protecting groups mentioned under process a). The protecting groups are preferably introduced in the manner described hereinafter under "General process conditions".

A nucleofugal leaving group X in a compound of formula (VI) is especially a leaving group selected from hydroxy esterified by a strong inorganic or organic acid, especially hydroxy esterified by a mineral acid, for example a hydrohalic acid, such as hydrochloric, hydrobromic or hydriodic acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, such as a methanesulfonic acid, p-bromobenzenesulfonic acid or p-toluenesulfonic acid, or hydroxy esterified by hydrazoic acid. The compound in question can also be prepared in situ by replacing a radical X, for example Cl, by a different radical X, for example I (preferably by an alkali metal iodide, such as NaI), and then reacting it further in the resulting reaction mixture.

In a starting material of formula (VI), X is preferably halogen, such as chlorine, bromine or iodine, especially bromine or iodine.

The reaction is preferably carried out in the presence of a strong base, such as an alkali metal hydride, for example sodium hydride or potassium hydride, or an alkali metal amide, such as sodium amide, or an alkali metal di-lower alkylamide, such as lithium diisopropylamide, especially in the presence of sodium hydride or potassium hydride, which can be added, for example, in the form of a dispersion in oil or after extraction of the oil, for example with a liquid hydrocarbon, such as hexane, using an equimolar amount, relative to the molar amount of the compound of formula (V), or preferably an excess of the base, for example an amount that is from 1 to 20 times, especially from 2 to 10 times, the molar amount, at preferred temperatures of from −10° C. to the reflux temperature of the reaction mixture, especially at from approximately 5° C. to approximately 60° C., or (where starting materials having phosphoryl-protected amino groups are used) at from 10° C. to reflux temperature, for example at from 20° C. to 80° C., in aprotic, especially polar, solvents, such as acid amides, for example dimethylformamide, diethylformamide, 1,3-dimethyl-3,4,5,6-tetrahydro-2(1H)-pyrimidinone (DMPU) or hexamethylphosphoric acid triamide, aromatic hydrocarbons, such as toluene or benzene (in which case preferably in the presence of a phase-transfer catalyst, for example a tetra-lower alkylammonium halide, such as tetra(n-butyl)ammonium bromide), ethers, for example cyclic ethers, such as dioxane, or mixtures of such solvents, in the presence or absence of a protecting gas, such as argon or nitrogen it being possible to remove the ammonia that is formed when alkali metal amides are used as bases by, for example, application of a vacuum, for example of from 0.1 to 100, especially from 0.5 to 10, torr.

The compound of formula (VI) is preferably used in an approximately equimolar amount or in excess relative to the compound of formula (V), especially in an amount that is from 1 to 20 times, especially from 2 to 5 times, the molar amount, relative to the compound of formula (V).

When the protecting group at the nitrogen atom to be alkylated by the compound of formula (VI) is an organic sulfonic acid radical, such as arylsulfonyl, especially phenylsulfonyl or lower alkylphenylsulfonyl, such as benzene- or toluene-sulfonyl, or aryl-lower alkylsulfonyl, especially phenyl- or lower alkylphenyl-lower alkylsulfonyl, such as benzyl- or 4-methylbenzyl-sulfonyl, the alkylation with a compound of formula (VI) can preferably be carried out in the presence of weaker bases, such as especially metal hydroxides or carbonates, such as especially alkali metal hydroxides, for example sodium or potassium hydroxide, or alkaline earth metal carbonates or alkali metal carbonates, for example sodium or potassium carbonate, preferably in the last-mentioned solvents, especially in halogenated hydrocarbons, such as dichloromethane or chloroform, and more especially in carboxylic acid amides, such as dimethylformamide or dimethylacetamide, and at the temperatures indicated and preferably under a protecting gas, such as nitrogen or argon.

The removal of the protecting groups, especially of the tert-butoxycarbonyl protecting group, from the resulting protected compounds of formula (I) is preferably carried out under the conditions described under process a).

A starting material of formula (V) containing protected primary and secondary amino groups corresponds to a protected starting material of formula (IX) mentioned above under process a), wherein $R_3$ is N-protected 2-(2-piperidyl)-ethyl and m is 3 or 4, and is obtainable in the manner described therein.

A starting material of formula (VI) containing protected secondary amino groups corresponds to a protected starting material of formula (X) mentioned above under process a), wherein $R_4$ is as defined, n is as defined for compounds of formula (II) and X is a nucleofugal leaving group as defined more precisely above under process b) for compounds of formula (IV), and is obtainable in the manner described therein.

Of course, the proviso of process a) that at least one 2-pyridyl radical must be present does not apply in respect of the compounds of formulae (V) and (VI) and the starting materials.

Process d) (nucleophilic substitution)

In the piperidyl compound of formula (VII) and the compound of formula (VIII), the nitrogen atoms are each in monoprotected form (one bond to a protecting group per nitrogen atom). There come into consideration as protecting groups especially the amino-protecting groups mentioned under process a). The protecting groups are preferably introduced in the manner described hereinafter under "General process conditions".

A nucleofugal leaving group X in a compound of formula (VIII) is especially a leaving group selected from hydroxy esterified by a strong inorganic or organic acid, especially hydroxy esterified by a mineral acid, for example a hydrohalic acid, such as hydrochloric, hydrobromic or hydriodic acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, such as a methanesulfonic acid, p-bromotoluenesulfonic acid or p-toluenesulfonic acid, or hydroxy esterified by hydrazoic acid. The compound in question can also be prepared in situ by replacing a radical X, for example Cl, by a different radical X, for example I (preferably by an alkali metal iodide, such as NaI), and then reacting it further in the resulting reaction mixture.

In a starting material of formula (VIII), X is preferably halogen, such as chlorine, bromine or iodine, especially bromine or iodine.

The reaction is preferably carried out in the presence of a strong base, such as an alkali metal hydride, for example sodium hydride or potassium hydride, or an alkali metal amide, such as sodium amide, or an alkali metal di-lower alkylamide, such as lithium diisopropylamide, especially in the presence of sodium hydride or potassium hydride, which can be added, for example, in the form of a dispersion in oil or after extraction of the oil, for example with a liquid hydrocarbon, such as hexane, using an equimolar amount, relative to the molar amount of the compound of formula (VII), or preferably an excess of the base, for example an amount that is from 1 to 20 times, especially from 2 to 10 times, the molar amount, at preferred temperatures of from −10° C. to the reflux temperature of the reaction mixture, especially at from approximately 5° C. to approximately 60° C., or (where starting materials having phosphoryl-protected amino groups are used) at from 10° C. to reflux temperature, for example at from 20° C. to 80° C., in aprotic, especially polar, solvents, such as acid amides, for example dimethylformamide, diethylformamide, 1,3-dimethyl- 3,4,5,6-tetrahydro-2(1H)-pyrimidinone (DMPU) or hexamethylphosphoric acid triamide, aromatic hydrocarbons, such as toluene or benzene (in which case preferably in the presence of a phase-transfer catalyst, for example a tetra-lower alkylammonium halide, such as tetra(n-butyl)ammonium bromide), ethers, for example cyclic ethers, such as dioxane, or mixtures of such solvents, in the presence or absence of a protecting gas, such as argon or nitrogen; it being possible to remove the ammonia that is formed when alkali metal amides are used as bases by, for example, application of a vacuum, for example of from 0.1 to 100, especially from 0.5 to 10, torr.

The compound of formula (VIII) is preferably used in an approximately equimolar amount or in excess relative to the compound of formula (VII), especially in an amount that is from 1 to 20 times, especially from 2 to 5 times, the molar amount, relative to the compound of formula (VII).

When the protecting group at the nitrogen atom in the compound of formula (VII) that is to be alkylated by the compound of formula (VIII) is an organic sulfonic acid radical, such as arylsulfonyl, especially phenylsulfonyl or lower alkylphenylsulfonyl, such as benzene- or toluenesulfonyl, or aryl-lower alkylsulfonyl, especially phenyl- or lower alkylphenyl-lower alkylsulfonyl, such as benzyl- or 4-methylbenzyl-sulfonyl, the alkylation with a compound of formula (VIII) can preferably be carried out in the presence of weaker bases, such as especially metal hydroxides or carbonates, such as especially alkali metal hydroxides, for example sodium or potassium hydroxide, or alkaline earth metal carbonates or alkali metal carbonates, for example sodium or potassium carbonate, preferably in the last-mentioned solvents, especially in halogenated hydrocarbons, such as dichloromethane or chloroform, and more especially in carboxylic acid amides, such as dimethylformamide or dimethylacetamide, and at the temperatures indicated and preferably under a protecting gas, such as nitrogen or argon.

The removal of the protecting groups, especially of the tert-butoxycarbonyl protecting group, from the resulting protected compounds of formula (I) is preferably carried out under the conditions described under process a).

Protected 2-(2-aminoethyl)-piperidine of formula (VII) can be prepared from 2-(2-amino-ethyl)-pyridine, which can be prepared by known processes or is available commercially (for example from Aldrich, Buchs, Switzerland), by hydrogenation under conditions analogous to the conditions mentioned under process a) for the hydrogenation of compounds of formula (II) and by subsequent introduction of protecting groups analogously to the conditions likewise mentioned therein.

Compounds of formula (VIII) can be prepared by processes known per se. For example, a compound of formula (VIII) can be obtained from a compound of formula (VI), as defined under process c), and a compound of formula (XV),

$$HO-(CH_2)_m-NH_2 \qquad (XV)$$

wherein m is 3 or 4 and the hydroxy group is in protected form (the introduction of hydroxy-protecting groups, their nature and the removal thereof are described hereinafter under "General process conditions") under reaction conditions analogous to those mentioned for the reaction of compounds of formulae (III) and (IV), with nucleophilic substitution, amino-protecting groups can be introduced under conditions analogous to those described under process a), and then the hydroxy-protecting group can be removed and the radical X can be introduced in a manner analogous to that described in the preparation of compounds of formula (X) from compounds of formula (XII).

Compounds of formula (XV) are known and are available, for example, commercially (for example from Aldrich, Buchs, Switzerland).

Additional process measures (to be carried out if desired): Conversion of salts and separation of isomers The conversion of a salt of a compound of formula (I) into a free compound of formula (I) or into a different salt is carried out, for example, in solvents, especially in organic solvents, more especially in polar organic solvents, most especially in esters, for example lower alkanoyl-lower alkyl esters, such as ethyl acetate, in amides, for example N,N-di-lower alkyl-lower alkanoylamides, such as dimethylformamide, in alcohols, for example hydroxy-lower alkanes, such as methanol, ethanol, ethylene glycol or glycerol, or aryl alcohols, such as phenols, for example phenol, or in dimethyl sulfoxide, in the absence or presence of water, preferably in the presence of water, or in water itself. Special preference is given to reaction in alcohols, such as the last-mentioned hydroxy-lower alkanes, in mixtures of such alcohols and water, or in water itself.

The conversion is carried out, for example, in free solution, but it can also be effected on chromatographic columns, for example by gel filtration, on ion exchangers or using semi-permeable membranes by osmotic processes, for example by dialysis.

The conversion is carried out at temperatures from the freezing point to the boiling point of the solutions in question, preferably at from 0° C. to 50° C., especially at from 20° C. to 40° C., for example at room, temperature, in the presence or absence of a protecting gas, such as nitrogen or argon.

In the case of conversion into different salts, the compound of formula (I) and the salt-forming acid are used in suitable molar ratios, or the acid is employed in excess. Preferably, the individual components are used in the molar ratio that corresponds to the ratio of the molarity of the base of formula (I) and of the acid in the resulting salts.

The salts that are formed precipitate, for example, by themselves, in some cases only after cooling, or they are precipitated by the addition of solvents, especially of non-polar solvents, for example ether, such as diethyl ether, or of water, and/or are obtained by partial or complete concentration by evaporation.

The reaction can also be effected via the free bases of formula (I), which are prepared, for example, by converting the acid salt, used as starting material, of a base of formula (I) into the free base with a first acid and with the aid of a base, for example a hydroxy base, such as an alkali metal hydroxide, for example NaOH or KOH, or with an OH⁻-charged ion exchanger in aqueous solution in the presence or absence of an organic solvent, as defined above; the subsequent conversion of the free base is carried out, for example, in the manner described above.

Mixed salts can be obtained, for example, when compounds of formula (I) are lyophilized from buffer solutions.

The preparation of the free bases of the compounds of formula (I) from corresponding salts is preferably carried out in the manner just described, also by chromatography, for example by gel filtration, or on ion exchangers.

Mixtures of isomers obtainable according to the invention can be separated into the individual isomers in a manner known per se; diastereoisomers can be separated, for example, by partitioning between polyphasic solvent mixtures, recrystallization and/or separation by chromatography, for example on silica gel, and racemates can be separated, for example, by the formation of salts with optically pure salt-forming reagents and separation of the mixture of diastereoisomers so obtainable, for example by means of fractional crystallization, or by chromatography on optically active column materials.

General process conditions

The following applies in general to all processes mentioned hereinbefore and hereinafter:

Unless a specific method of synthesis is indicated for starting materials, the starting materials are known, can he prepared by processes known per se and/or are available commercially.

In view of the close relationship between the compounds of formula (I) and their salts and starting materials (starting materials and intermediates) in free form and in the form of their salts, any reference hereinbefore and hereinafter to the free compounds or their salts is to be understood as meaning also the corresponding salts or free compounds, respectively, where appropriate and expedient.

All the process steps mentioned above can be carried out under reaction conditions that are known per se, preferably those mentioned specifically, in the absence or, customarily, in the presence of solvents or diluents, preferably solvents or diluents that are inert towards the reagents used and are solvents therefor, in the absence or presence of catalysts, condensation agents or neutralizing agents, for example ion exchangers, such as cation exchangers, e.g. in the $H^+$ form or the $OH^-$ form, depending upon the nature of the reaction and/or of the reactants at reduced, normal or elevated temperature, for example in a temperature range of from approximately $-100°$ C. to approximately $190°$ C., preferably from approximately $-80°$ C. to approximately $150°$ C., for example at from $-80°$ C. to $-60°$ C., at room temperature, at from $-20°$ C. to $40°$ C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Conversion of salts and separation of isomers,".

The solvents from which those solvents that are suitable for any particular reaction can be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitrites, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless indicated otherwise in the description of the processes. Such solvent mixtures can also be used in working up, for example by chromatography or partitioning.

The compounds, including their salts, can also be obtained in the form of hydrates, or their crystals can, for example, include the solvent used for crystallizsation.

If necessary, protected starting materials can be used in all process steps and the protecting groups can be removed at suitable stages of the reaction.

When several protected functional groups are present, the protecting groups may, if desired, be so selected that it is possible to remove more than one such group simultaneously. Conversely, the groups may also be so selected that they cannot all be removed simultaneously but can be removed in a desired sequence, in which case the corresponding intermediates are obtained.

The introduction of amino-protecting groups that is necessary for the preparation of protected starting materials is carried out in a manner known per se, for example in the manner described in the standard works mentioned hereinbefore under process a), and can be carried out stepwise or, preferably, in a single procedure.

For the introduction of the acyl protecting group of a carbonic acid semiester, such as lower alkoxycarbonyl, there are suitable especially symmetrical or mixed carbonic acid anhydrides, such as di-lower alkyl dicarbonate, for example di-tert-butyl dicarbonate, or lower alkoxycarboxylic acid azides, such as tert-butoxycarboxylic acid azide, or other activated carbonic acid semiester derivatives, such as imidazolide, for example lower alkoxy-, such as tert-butoxycarboxylic acid 1-imidazolide, or 2-(tert-butoxycarbonyloxyimino)-2-phenylacetonitrile, especially di-tert-butyl dicarbonate.

For the introduction of organic sulfonic acid radicals, such as arylsulfonic acid radicals, especially phenylsulfonyl radicals or mono-, di- or tri-lower alkylphenylsulfonyl radicals, such as benzene-, toluene- or mesitylene-sulfonyl, or lower alkylsulfonyl radicals, there are suitable especially corresponding sulfonyl halides, such as sulfonyl chlorides or bromides, for example toluenesulfonic acid chloride.

For the introduction of suitable organic phosphoryl radicals, such as diarylphosphinyl, especially diphenylphosphinyl, or especially di(lower alkoxy) phosphoryl, such as diethoxyphosphoryl, there is suitable especially reaction with corresponding phosphoryl halides, for example phosphoryl chlorides, such as diphenylphosphinyl chloride (see Osborn, H. M. I., et al., Synlett 2, 145–147 (1994)), or phosphoryl iodides, such as di-lower alkoxyphosphoryl iodide (which can be prepared, for example, electrochemically in situ in acetonitrile on platinum electrodes in supporting electrolytes, such as tetra-lower alkylammonium halides, for example tetraethylammonium bromide, see J. Gen. Chem. (USSR) 62, 370 (1992)); or (for the introduction especially of di(lower alkoxy)phosphoryl) from the corresponding phosphites, such as di(lower alkyl) phosphite, especially diethyl phosphite, under substantially anhydrous conditions, for example by phase-transfer catalyst in the presence of a. phase-transfer catalyst, for example of a tetra-lower alkylammonium halide, such as tetra(n-butyl)ammonium bromide; in the presence (in each case preferably in excess, for example in a 2- to 20-fold molar excess, relative to the base to be protected) of a dehydrating inorganic salt, such as potassium carbonate, and of a base that can be converted by the phase-transfer catalyst from the solid form into the organic solution, such as potassium hydrogen carbonate; in suitable organic solvents or solvent mixtures, such as halogenated hydrocarbons, for example methylene chloride or carbon tetrachloride, or mixtures thereof; at preferred temperatures of from $0°$ C. to $40°$ C., for example at from approximately $10°$ C. to approximately $30°$ C. (see J. Org. Chem. 56, 4904–4907 (1991)); reaction without a phase-transfer catalyst also being possible.

For the introduction of divalent amino-protecting groups, such as unsubstituted or mono- or di-substituted methylene groups, such as 1-lower alkoxy (for example methoxy or ethoxy)-lower alkylene (;or example ethylene or 1-n- butylene), for example —C(CH$_3$)(OC$_2$H$_5$)—, conventional methods are used. Especially for the introduction of mono- or di-lower alkyl- or phenyl-methylene, for example —C(CH$_3$)$_2$— or —CH(-phenyl)-, especially —CH$_2$—, there are suitable corresponding aldehydes or ketones in which there is an oxo group in place of the two bonds indicated in the formulae shown above, for example benzaldehyde or especially acetone or more especially formaldehyde.

The introduction is carried out under customary conditions, preferably in solvents, such as carboxylic acid amides, for example dimethyl- or diethyl-formamide, in chlorinated hydrocarbons, such as carbon tetrachloride, chloroform or methylene chloride, or in ethers, such as cyclic ethers, for example tetrahydrofuran, or mixtures thereof, in the case of the introduction of sulfonyl radicals additionally in the presence of water (biphasic system) and in the case of the introduction of unsubstituted, mono- or di-substituted methylene groups also if desired additionally or exclusively in the presence of water, it being possible in each case for the water to contain a base, such as an alkali metal hydroxide, such as sodium or potassium hydroxide, if necessary under a protecting gas, such as nitrogen or argon, and if necessary in the presence of bases, such as tertiary nitrogen bases, for example triethylamine, pyridine or 4-dimethylaminopyridine, or of morpholine, or hydroxides, such as ammonium hydroxide or alkali metal hydroxides, for example sodium or potassium hydroxide.

Preferred temperatures are from −10° C. to 50° C., especially from 0° C. to 30° C.

A hydroxy group present in a starting material can, if necessary, be protected by protecting groups. Protecting groups are introduced and removed at suitable times.

A hydroxy group can be protected, for example, by a monovalent protecting group, such as an acyl group, for example lower alkanoyl that is unsubstituted or substituted by halogen, such as chlorine, such as acetyl or 2,2-dichloroacetyl, or especially by an acyl radical of a carbonic acid semiester mentioned for protected amino groups. A preferred hydroxy-protecting group is, for example, 2,2,2-trichloroethoxycarbonyl, 4-nitrobenzyloxycarbonyl or diphenylmethoxycarbonyl. A hydroxy group can also be protected by tri-lower alkylsilyl, for example trimethylsilyl, triisopropylsilyl, tert-butyl-dimethylsilyl or especially dimethyl-(2,3-dimethyl-2-butyl)silyl (=tert-hexyl-dimethylsilyl), by a readily removable etherifying group, for example an alkyl group, such as tert-lower alkyl, for example tert-butyl, by an oxa- or thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or l-ethylthioethyl, or by 2-oxa- or 2-thia-cycloalkyl having from 5 to 7 ring atoms, such as 2-tetrahydrofuryl or 2-tetrahydropyranyl, or by a corresponding thia analogue, as well as by 1-phenyl-lower alkyl, such as benzyl, diphenylmethyl or trityl, wherein the phenyl radicals can be unsubstituted or substituted, for example, by halogen, e.g. chlorine, lower alkoxy, e.g. methoxy, and/or by nitro.

A protected hydroxy group is preferably protected by lower alkoxycarbonyl or tri-lower alkylsilyl, especially by trimethylsilyl, tert-butyl-dimethylsilyl, dimethyl-(2,3-dimethyl-2-butyl)silyl or tert-butoxycarbonyl.

Hydroxy-protecting groups, where required, are introduced into the starting materials by methods known per se. Examples of suitable reaction conditions are described, for example, in the above-mentioned standard works of J. F. W. McOmie and T. W. Greene and P. G. M. Wuts.

For example, a tri-lower alkylsilyl protecting group is converted into a hydroxy group protected by tri-lower alkylsilyl by reaction of the hydroxy group in a starting material with a tri-lower alkylsilyl halide, such as a tri-lower alkylsilyl chloride, in an inert solvent, such as a lower alkyl cyanide, for example acetonitrile, in the presence of a tertiary nitrogen base, such as 1,8-diazabicyclo[5.4.0]undec-7-ene, at temperatures of from 0° C. to 50° C., especially from 15° C. to 30° C.

Hydroxy-protecting groups are removed at suitable times, for example as follows:

A hydroxy group protected by a suitable acyl group or by unsubstituted or substituted 1-phenyl-lower alkyl is freed analogously to a correspondingly protected amino group. A hydroxy group protected by 2,2-dichloroacetyl is freed, for example, by basic hydrolysis, and a hydroxy group protected by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid.

Tri-lower alkylsilyl, such as trimethylsilyl or dimethyl-(2,3-dimethyl-2-butyl)silyl, is preferably removed by solvolysis, for example with alcohols, such as methanol or ethanol, at temperatures of from 20° C. to reflux temperature. A tri-lower alkylsilyl group is also removed by acidolysis with a mineral acid, especially hydrofluoric acid, or a strong carboxylic acid, such as trifluoroacetic acid, or by reaction with the fluoride salt of a metal or a base that frees fluoride ions, for example the acid addition salt of hydrogen fluoride and a nitrogen base or a metal fluoride, such as an alkali metal fluoride, for example sodium or potassium fluoride, in the absence or presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride, tetrabutylammonium fluoride or N-benzyl-trimethylammonium fluoride, in the presence of aprotic polar solvents, such as ethers, for example tetrahydrofuran or dioxane, dimethyl sulfoxide or N,N-dimethylacetamide, at preferred temperatures of approximately from −20° C. to 50° C., for example from 0° C. to room temperature.

2-Halo-lower alkoxycarbonyl as a hydroxy-protecting group is removed by means of reducing agents, for example a reducing metal, such as zinc, reducing metal salts, such as chromium(II) salts, or by means of sulfur compounds, for example sodium dithionite or preferably sodium sulfide and carbon disulfide.

The introduction and removal of tri-lower alkylsilyl as a hydroxy-protecting group, as described above, is especially preferred, especially where amino groups present in the molecule are protected by the radical of a carbonic acid semiester, especially lower alkoxycarbonyl.

Unless any specific methods are indicated, starting materials can be prepared analogously to the processes mentioned above, are known, can be prepared by processes known per se, or are available commercially.

Where indicated, the reaction conditions mentioned specifically in each particular case are preferred.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention there are preferably used those starting materials which result in the compounds of formula (I) described at the beginning as being especially valuable. The present invention relates also to novel starting materials. Reaction conditions that are analogous to those mentioned in the Examples are especially preferred.

Pharmaceutical compositions and processes

The present invention relates also to pharmaceutical compositions that comprise compounds of formula (I) as active ingredient. Compositions for enteral, especially oral, and parenteral administration are especially preferred. The compositions comprise the active ingredient on its own or, preferably, together with a pharmaceutically acceptable carrier. The dose of active ingredient depends upon the disease to be treated, and upon the species, its age, weight and individual condition, and upon the mode of administration.

Preference is given to a pharmaceutical composition that is suitable for administration to a warm-blooded animal, especially a human, suffering from a disease that is responsive to a reduction in the intracellular concentration of natural polyamines, such as especially putrescine, spermidine and spermine, especially one of the diseases mentioned hereinbefore, for example tumor diseases, opportunistic infections or protozoal infections, which composition comprises a compound of formula (I) or a salt thereof in an amount that is effective in the treatment of the mentioned diseases, together with at least one pharmaceutically acceptable carrier.

The pharmaceutical compositions comprise from approximately 5% to approximately 95% active ingredient, dosage forms that are in single dose form preferably comprising from approximately 20% to approximately 90% active ingredient, and dosage forms that are not in single dose form preferably comprising from approximately 5% to approximately 20% active ingredient. Unit dose forms, such as dragées, tablets or capsules, comprise from approximately 0.05 g to approximately 1.5 g of active ingredient.

The pharmaceutical compositions of the present invention are prepared in a manner known per se, for example by means of conventional mixing, granulating, confectioning, dissolving or lyophilizing processes. For example, pharmaceutical compositions for oral administration can be obtained by combining the active ingredient with one or more solid carriers, optionally granulating a resulting mixture, and processing the mixture or granules, if desired, where appropriate by the addition of additional excipients, to form tablets or dragée cores.

Suitable carriers are especially fillers such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches and also carboxymethyl starch, cross-linked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions, which may comprise gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Colorings or pigments may be added to the tablets or dragée coatings, for example for identification purposes or to indicate different doses of active ingredient.

Pharmaceutical compositions; for oral administration are also hard gelatin capsules, and soft sealed capsules consisting of gelatin and a plasticizer, such as glycerol or sorbitol. The hard gelatin capsules may contain the active ingredient in the form of granules, for example in admixture with fillers, such as corn starch, binders and/or glidants, such as talc or magnesium stearate, and, where appropriate, stabilizers. In soft capsules the active ingredient is preferably dissolved or suspended in suitable liquid excipients, for example aqueous solutions, fatty oils, such as sesame oil, fatty acid esters of the ethylene glycol or propylene glycol type, such as ®Lauroglycol (1,2-propylene glycol monolaurate, as a mixture of the two constitutional isomers; Gattefossé S. A., Saint Priest, France), ®Gelucire (glycerides and partial polyglycerides of fatty acids; Gattefossé S. A., Saint Priest, France) or sesame oil, paraffin oil or liquid polyethylene glycols, such as PEG 300 or 400 (Fluka, Switzerland), it likewise being possible to add stabilizers or pharmaceutically acceptable detergents.

Other oral dosage forms are, for example, syrups prepared in customary manner which comprise the active ingredient, for example, in dispersed form and in a concentration of approximately from 5% 20%, preferably approximately 10% or in a similar concentration that provides a suitable single dose when administered, for example, in a measure of 5 or 10 ml. Also suitable are, for example, powdered or liquid concentrates for the preparation of shakes, for example in milk. Such concentrates may also be packed in single dose quantities.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that include viscosity-increasing substances, for example sodium carboxymethylcellulose, sorbitol and/or dextran, and, if desired, stabilizers. The active ingredient, where appropriate together with excipients, can also be in the form of a lyopholizate and be made into a solution prior to parenteral administration by the addition of suitable solvents.

Solutions used, for example, for parenteral administration can also be used as infusion solutions.

The invention relates also to a process or a method for the treatment of the above-mentioned pathological conditions, especially those which are responsive to a reduction in the intracellular concentration of polyamines. The compounds of the present invention can be administered prophylactically or therapeutically, preferably in an amount that is effective against the mentioned diseases, to a warm-blooded animal, for example a human or a commercially valuable mammal, requiring such treatment, the compounds preferably being used in the form of pharmaceutical compositions. For a body weight of approximately 70 kg, a daily dose of from 1 mg to 8000 mg, for example from approximately 0.1 g to approximately 7 g, preferably from approximately 0.5 g to approximately 5 g, of a compound of the present invention is administered.

EXAMPLES

The Examples which follow serve to illustrate the invention, but do not limit the scope thereof in any way.

Temperatures are given in degrees Celsius.

Where ratios of the components of solvent mixtures are given, the ratios are always by volume (v/v).

The following abbreviations are used: BOC=tert-butoxycarbonyl; DMF=N,N-dimethylformamide; hexane=n-hexane; $^1$H-NMR=$^1$H nuclear magnetic resonance spectroscopy (indication of the chemical shift in ppm as the δ value); $R_f$=ratio of the seepage propagation of a compound to the seepage propagation of the solvent front (ratio of fronts) in thin-layer chromatography; brine=saturated sodium chloride solution.

Example 1

1-Ethyl-9-[2-(2-piperidyl)-ethyl]-1,5,9-triazanonane tetrahydrochloride 0.18 g of rhodium oxide/platinum oxide (Nishimura catalyst) is added to a solution of 0.54 g (0.956 mmol) of 1-ethyl-9-[2-(2-pyridyl)-ethyl]-1,5,9-tri-BOC-1,5,9-triazanonane in 20 ml of methanol, and hydrogenation is carried out in a temperature range of from 20° C. to 50° C. until the absorption of hydrogen has ceased. The catalyst is then filtered off, the filtrate is concentrated to a volume of approximately 2 ml, 15 ml of 3N methanolic hydrochloric acid are added, and the mixture is stirred at 20° C. for 15 hours. The resulting title compound is isolated by filtration and recrystallized from ethanol, m.p. >250° C. $^1$H-NMR (D$_2$O): δ =1.22(t,3H); 1.33–1.73(m,3H); 1.73–2.15(m,9H); 2.88–3.41(m,15H).

The starting materials are prepared as follows:

a) 1-Ethyl-9-[2-(2-pyridyl)-ethyl]-1,5,9-tri-BOC-1,5,9-triazanonane

To a solution of 1.85 g (5.1 mmol) of N,N'-di-BOC-N-[2-(2-pyridyl)-ethyl]-1,3-propanediamine in 20 ml of dioxane there are added, with stirring, 0.4 g (10 mmol) of sodium hydride dispersion (approximately 60% in oil; Fluka, Buchs, Switzerland) and, after 20 minutes, a solution of 1.23 ; (6 mmol) of N-BOC-N-ethyl-3-bromo-propylamine in 2 ml of dioxane. The reaction mixture is stirred at 50° C. for 18 hours, a further 0.4 g (10 mmol) of sodium hydride dispersion (approximately 60%) and 1.23 g (6 mmol) of N-BOC-N-ethyl-3-bromo-propylamine are added at 25° C., the mixture is stirred at 50° C. for a further 18 hours and is then coded to room temperature, 50 ml of water are added, and the reaction mixture is extracted with methylene chloride. The methylene chloride extract is dried over sodium sulfate and concentrated by evaporation. and the residue is purified by flash chromatography on silica gel having a particle size of 0.04–0.063 mm using tert-butyl methyl ether. After concentration of the product-containing fractions by evaporation, the title compound is obtained in the form of an oil, $R_f$ value=0.37 (silica gel/tert-butyl methyl ether).

b) N,N'-Di-BOC-N-[2-(2-pyridyl)-ethyl]-1,3-propanediamine and N,N'-Di-BOC-N,N'-bis[2-(2-pyridyl)-ethyl]-1,3-propanediamine A mixture of 6.5 ml (0.0779 mol) of 1,3-propanediamine (Aldrich, Buchs, Switzerland), 12 ml of water and 19.5 ml (0.1716 mol) of 2-vinylpyridine (95%; Fluka, Buchs, Switzerland) is heated at 100° C. for 10 hours, with stirring. The emulsion is cooled to room temperature and a solution of 35 g (0.16 mol) of di-tert-butyl dicarbonate in 60 ml of methylene chloride is then added dropwise thereto. After 2 hours' stirring at 20° C., the reaction mixture is concentrated by evaporation in vacuo and the residue is purified by flash chromatography on silica gel having a particle size of 0.04–0.063 mm using methylene chloride, tert-butyl methyl ether and tert-butyl methyl ether/methanol (9:1). The product-containing fractions are concentrated by evaporation, yielding the first title compound mentioned [$R_f$ value=0.57 (silica gel/tert-butyl methyl ether:methanol (9:1))] and the second title compound mentioned [$R_f$ value=0.35 (silica gel/tert-butyl methyl ether:methanol (9:1))] in the form of oils.

c) N-BOC-N-ethyl-3-bromo-propylamine 11 g (0.0618 mol) of N-bromosuccinimide are added in the course of 5 minutes, with stirring, to a solution, which has been cooled to 0° C., of 10.49 g (0.0516 mol) of 3-(N-BOC-ethylamino)-1-propanol and 16.23 g (0.0619 mol) of triphenylphosphine in 160 ml of methylene chloride. The reaction mixture is stirred for a further 30 minutes at 0°–20° C. and is then concentrated by evaporation in vacuo. The dark-colored oily residue is stirred with 200 ml of hexane, whereupon a brown precipitate forms. After filtration and concentration of the filtrate by evaporation in vacuo, the title compound is obtained in the form of an oil, $R_f$ value=0.71 (silica gel/tert-butyl methyl ether).

d) 3-(N-BOC-ethylamino)-1-propanol 12.6 g (0.05773 mol) of di-tert-butyl dicarbonate are dissolved in 60 ml of methylene chloride and added dropwise in the course of 30 minutes, with stirring, to a solution of 5.5 g (0.05331 mol) of 3-ethylamino-1-propanol (J. Am. Chem. Soc. 80, 5203 (1958)) in 20 ml of methylene chloride. The reaction mixture is stirred at room temperature for 15 hours and is then concentrated by evaporation in vacuo. The oily residue is dissolved in 25 ml of methanol saturated with ammonia and the mixture is left to stand at room temperature for 15 minutes and is then concentrated by evaporation in vacuo at 40° C. The residue that is obtained is the crude title compound in the form of a colorless oil, $R_f$ value=0.12 (silica gel/tert-butyl methyl ether).

Example 2

N,N'-Bis[2-(2,-piperidyl)-ethyl]-1,3-propanediamine tetrahydrochloride 0.5 g of platinum dioxide (Adams catalyst) is added to a solution of 2 g (4.13 mmol) of N,N'-di-BOC-N,N'-bis[2-(2-pyridyl)-ethyl]-1,3-propanediamine (see Example 1b) in 20 ml of methanol, and hydrogenation is carried out for 26 hours in a temperature range of from 20° C. to a maximum of 52° C. and under normal pressure. After the addition of 0.2 g of rhodium oxide/platinum oxide (Nishimura catalyst), hydrogenation is carried out for a further 2 hours at 50° C. until the absorption of hydrogen has ceased. The catalyst is then filtered off, the filtrate is concentrated to a volume of approximately 4 ml, 18 ml of 3N methanolic hydrochloric acid are added, and the mixture is left to stand at 8° C. for 15 hours. The resulting title compound is isolated by filtration and recrystallized from methanol, m.p. >250° C., water content: 6.42%. $^1$H-NMR (D$_2$O): δ =1.32–1.75(m,6H); 1.75–2.16(m,12H); 2.88–3.41(m,14H).

Example 3

1-Propyl-9-[2-(2-piperidyl)-ethyl]-1,5,9-triazanonane tetrahydrochloride 30 ml of 3N methanolic hydrochloric acid are added to a solution of 2.07 g (3.54 mmol) of 1-propyl-9-[2-(2- piperidyl)-ethyl]-1,5,9-tri-BOC-1,5,9-triazanonane in 5 ml of methanol, and the reaction mixture is stirred at room temperature for 15 hours. The crystallisate is filtered off and the filtration residue is suspended in 15 ml of hot methanol. After cooling to room temperature, filtration, washing the crystallizate with ice-cold methanol and drying under a high vacuum at 100° C., the title compound is obtained, m.p. >270° C. $^1$H-NMR (D$_2$O): δ =0.92(t,3H); 1.41–2.18(m, 14H); 2.90–3.42(m,15H).

The starting materials are prepared as follows:

a) 1-Propyl-9-[2-(2-piperidyl)-ethyl ]- 1,5,9-tri-BOC- 1,5, 9-triazanonane

A mixture of 2.084 g (3.6 mmol) of 1-propyl-9-[2-(2-pyridyl)-ethyl]-1,5,9-tri-BOC-1,5,9-triazanonane, 20 ml of methanol and 0.2 g of pre-hydrogenated rhodium oxide/ platinum oxide (Nishimura catalyst) is hydrogenated at room temperature and under normal pressure until the absorption of hydrogen has ceased. After filtration and washing the catalyst with methanol, the filtrate is concentrated by evaporation in vacuo, yielding the title compound in the form of a colorless resin, $R_f$ value=0.51 (silica gel/tert-butyl methyl ether).

b) 1-Propyl-9-[2-(2-pyridyl)-ethyl]-1 5,9-tri-BOC- 1,5,9-triazanonane

To a solution of 3 g (5.59 mmol) of 1-[2-(2-pyridyl)-ethyl]-1,5,9-tri-BOC-1.5,9-triazanonane in 30 ml of DMF there are added, with stirring, 0.448 g (11.2 mmol) of sodium hydride dispersion (approximately 60%) and after 10 minutes, 1.02 ml (11.2 mmol) of 1-bromopropane. The reaction mixture is stirred at room temperature for 4 hours, at 40° C. for 18 hours and at 50° C. for 24 hours and is then concentrated by evaporation in vacuo, and the residue is partitioned between brine and methylene chloride. The organic phase is washed with brine and dried over sodium sulfate and is then concentrated by evaporation, and the residue is purified by flash chromatography on silica gel having a particle size of 0.04–0.063 mm using tert-butyl methyl ether/hexane mixtures (1:1 and 7:3). After concentration of the product-containing fractions by evaporation, the title compound is obtained in the form of a resin, $R_f$ value=0.50 (silica gel/tert-butyl methyl ether).

c) 1-[2-(2-Pyridyl)-ethyl]-1,5,9-tri-BOC-1,5,9-triazanonane

A mixture of 12.2 ml (0.0863 mol) of bis(3-aminopropyl) amine (Fluka, Buchs, Switzerland), 11.36 ml (0.1 mol) of 2-vinylpyridine (approximately 95%), 10 ml of water and 10 ml of glacial acetic acid is heated at 100° C. for 1.5 hours, with stirring, and is then cooled to room temperature, rendered basic with 2N sodium hydroxide solution and concentrated in vacuo at 50° C. The residue is then partitioned between 100 ml of methylene chloride and 150 ml of 2N sodium hydroxide solution, and a solution of 70 g (0.32 mol) of di-tert-butyl dicarbonate in 150 ml of methylene chloride is added dropwise to the two-phase mixture, with vigorous stirring. After 15 hours' stirring at 20° C., 10 ml of 30% sodium hydroxide solution are added to the reaction mixture and stirring is continued for a further 3 hours The organic phase is then separated off, washed with brine, dried over sodium sulfate, filtered and concentrated by evaporation. The residue is purified by flash chromatography on silica gel having a particle size of 0.04–0.063 mm using tert-butyl methyl ether as eluant. After concentration of the product-containing fractions by evaporation, the title compound is obtained in the form of a resin, $R_f$ value=0.17 (silica gel/methylene chloride:methanol (30:1))

Example 4

1-Allyl-9-[2-(2-piperidyl)-ethyl]-1,5,9-triazanonane tetrahydrochloride 20 ml of 3N methanolic hydrochloric acid are added to a solution of 0.94 g (1.376 mmol) of 1-allyl-9-[2-[(N-BOC)- 2-piperidyl]-ethyl]-1,5,9-tri-BOC-1,5,9-triazanonane in 5 ml of methanol, and the reaction mixture is stirred at room temperature for 15 hours. The crystallizate that has formed is isolated by filtration, washed with ice-cold methanol and dried under a high vacuum at 80° C. The resulting title compound melts at >280° C. $^1$H-NMR (D$_2$O): δ =1.40–2.18 (m,12H); 2.90–3.43(m,13H); 3.65(d,2H); 5.45–5.54(m,2H); 5.78–5.98(m,1H).

The starting materials are prepared as follows:

a) 1-Allyl-9-[2-[(N-BOC)-2-piperidyl]-ethyl]- 1,5,9-tri-BOC-1,5,9-triazanonane

To a solution of 1.13 g (1.758 mmol) of 1-[2-[(N-BOC) -2-piperidyl]-ethyl]-1,5,9-tri-BOC-1,5,9-triazanonane in 11.3 ml of DMF there are added, with stirring, 0.14 g (3.5 mmol) of sodium hydride dispersion (approximately 60%) and, after 10 minutes, 0.296 ml (3.5 mmol) of allyl bromide (Fluka, Buchs, Switzerland). The reaction mixture is stirred at room temperature for 15 hours and then a further ⅓ of the original amount of sodium hydride dispersion (approximately 60%) and a further ⅓ of the original amount of allyl bromide are added, the reaction mixture is stirred at room temperature for a further 24 hours and is then concentrated by evaporation in vacuo. The residue is partitioned between water and methylene chloride, and the organic phase is washed with brine, dried over sodium sulfate and concentrated by evaporation. After purification of the residue by flash chromatography on silica gel having a particle size of 0.04–0.063 mm using a hexane/tert-butyl methyl ether mixture (7:3), the title compound is obtained in the form of a resin, $R_f$ value=0.34 (silica gel/methylene chloride:methanol (30:1)).

b) 1-[2-[(N-BOC)-2-piperidyl]-ethyl]-1,5,9-tri-BOC-1,5,9-triazanonane

A mixture of 84.84 ml (0.6 mol) of bis(3-aminopropyl) amine, 11.36 ml (0.1 mol) of 2-vinylpyridine (approximately 95%) and 5.72 ml (0.1 mol) of glacial acetic acid is heated at 110° C. for 3 hours, with stirring, and is then cooled to room temperature. Excess or unreacted starting materials are separated from the reaction mixture by means of high-vacuum distillation at a bath temperature of from 20° C. to a maximum of 180° C., and the resinous distillation residue is suspended in a mixture of 200 ml of methanol and 40 ml of concentrated hydrochloric acid. After the addition of 1.9 g of pre-hydrogenated rhodium oxide/platinum oxide (Nishimura catalyst), hydrogenation is carried out at 26°–29° C. and under normal pressure until the absorption of hydrogen has ceased. 50 ml of methanol and water are then added to the reaction mixture, the catalyst is filtered off, and washing is then carried out with water. The filtrate is greatly concentrated using a rotary evaporator (water-jet vacuum) and the residue is partitioned, with stirring, between 300 ml of methylene chloride and excess 30% sodium hydroxide solution. A solution of 70.5 g (0.323 mol) of di-tert-butyl dicarbonate in 100 ml of methylene chloride is added dropwise to the resulting emulsion of crude 1-[2-(2-piperidyl)-ethyl]-1,5,9-triazanonane, and the reaction mixture is stirred for a further 15 hours at room temperature. The organic phase is then separated off and the aqueous phase is extracted with methylene chloride. After washing the combined organic phases with brine, drying over sodium sulfate and concentration by evaporation in vacuo, the oily residue is purified by flash chromatography twice on silica gel having a particle size of 0.04–0.063 mm using tert-butyl methyl ether or a hexane/tert-butyl methyl ether mixture (1:1). In that manner, the title compound is obtained in the form of an oil, $R_f$ value=0.26 (silica gel/methylene chloride:methanol (30:1)).

Example 5

1-Ethyl-9-[2-(2-piperidyl)-ethyl]-1,5,9-triazanonane tetrahydrochloride

To a solution of 5.25 g (8.2 mmol) of 1-[2-[(N-BOC)-2-piperidyl]-ethyl]-1,5,9-tri-BOC-1,5,9-triazanonane (see Example 4b) in 52 ml of DMF there are added, with stirring, 0.654 g (16.3 mmol) of sodium hydride dispersion (approximately 60%) and, after 10 minutes, 1.22 ml (16.3 mmol) of ethyl bromide. The reaction mixture is stirred at room temperature for 15 hours and is then concentrated by evaporation in vacuo. The residue is partitioned between water and methylene chloride and the organic phase is washed with brine, dried over sodium sulfite and concentrated by evaporation. The residue is purified by flash chromatography on silica gel having a particle size of 0.04–0.063 mm using a hexane/tert-butyl methyl ether mixture (7:3). The fractions containing the desired product are concentrated by evaporation and the resinous residue [1-ethyl-9-[2-[(N-BOC)-2-piperidyl]-ethyl]-1,5,9-tri-BOC-1,5,9-triazanonane, $R_f$ value=0.22 (silica gel/tert-butyl methyl ether:hexane (1:1))] is dissolved in 80 ml of 3N methanolic hydrochloric acid. The reaction mixture is stirred at room temperature for 15 hours and the crystallizate is isolated by filtration and washed with methanol. The title compound so obtained melts at >250° C. $^1$H-NMR ($D_2O$): $\delta$ =1.22(t,3H); 1.33–173(m,3H); 1.73–2.15(m,9H); 2.87–3.40 (m,15H)

Example 6

Capsules

Capsules comprising 1 g or active ingredient, that is to say a compound of formula I according to any one of Examples 1 to 5, are prepared as follows:

| Composition (for 1250 capsules): | |
|---|---|
| active ingredient | 1250 g |
| talc | 180 g |
| wheat starch | 120 g |
| magnesium stearate | 80 g |
| lactose | 20 g |

The powdered substances are pressed through a sieve having a mesh size of 0.6 mm and are mixed. 1.32 g portions of the mixture are introduced into gelatin capsules by means of a capsule-filling machine.

What is claimed is:
1. A compound of formula (I)

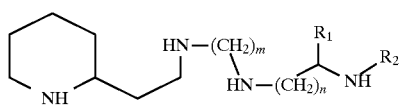

wherein either
  $R_1$ is hydrogen and
  $R_2$ is lower alkyl, lower alkenyl or lower alkynyl, with the proviso that the carbon atom of $R_2$ which is attached to the nitrogen atom is not part of a double bond,
  m is 3 or 4 and
  n is 2 or 3; or
  $R_1$ and $R_2$ together are tetramethylene,
  m is 3 or 4 and
  n is 2;
or a salt thereof.

2. A compound of formula (I) according to claim 1, wherein either
  $R_1$ is hydrogen and
  $R_2$ is lower alkyl or lower alkenyl,
  m is 3 or 4 and
  n is 2 or 3; or
  $R_1$ and $R_2$ together are tetramethylene,
  m is 3 or 4 and
  n is 2;
or a salt thereof.

3. A compound of formula (I) according to claim 1, wherein either
  $R_1$ is hydrogen and
  $R_2$ is lower alkyl or lower alkenyl; or
  $R_1$ and $R_2$ together are tetramethylene;
  m is 3 and
  n is 2;
or a salt thereof.

4. A compound of formula (I) according to claim 1, wherein
  $R_1$ is hydrogen and
  $R_2$ is lower alkyl,
  m is 3 and
  n is 2;
or a salt thereof.

5. A compound of formula (I) according to claim 1 wherein
  $R_1$ and $R_2$ together are tetaramethylene,
  m is 3 and
  n is 2;
or a salt thereof.

6. 1-Ethyl-9-[2-(2-piperidyl)-ethyl]-1,5,9-triazanonane of formula (I) according to claim 1, or a pharmaceutically acceptable salt thereof.

7. N,N'-Bis[2-(2-piperidyl)-ethyl]-1,3-propanediamine of formula (I) according to claim 1, or a pharmaceutically acceptable salt thereof.

8. 1-Propyl-9-[2-(2-piperidyl)-ethyl]-1,5,9-triazanonane of formula (I) according to claim 1, or a pharmaceutically acceptable salt thereof.

9. 1-Allyl-9-[2-(2-piperidyl)-ethyl]-1,5,9-triazanonane of formula (I) according to claim 1, or a pharmaceutically acceptable salt thereof.

10. A process for the preparation of a compound of formula (I), or a salt thereof, according to claim 1, which comprises
  a) for the preparation of compounds of formula (I) wherein $R_1$ is hydrogen and $R_2$ is lower alkyl, or $R_1$ and $R_2$ together are tetramethylene, reducing a pyridyl compound of formula (II)

wherein
  $R_3$ is 2-(2-piperidyl)-ethyl or 2-(2-pyridyl)-ethyl and either
  m is 3 or 4,
  n is 2 or 3 and R4 is a radical of formula (A)

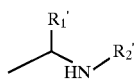

wherein
R$_1$' is hydrogen and
R$_2$' is lower alkyl, lower alkenyl or lower alkynyl; or
m is 3 or 4,
n is 2 and
R$_4$ is 2-piperidyl or 2-pyridyl,
wherein in the compound of formula (II)
(i) at least one of the two radicals R$_3$ and R$_4$ contains a 2-pyridyl radical, and
(ii) the nitrogen atoms can be free or completely or partially in protected form, to form a piperidyl compound, and removing any protecting groups that are present; or
b) for the preparation of compounds of formula (I) wherein R$_1$ is hydrogen, R$_2$ is lower alkyl, lower alkenyl or lower alkynyl m is 3 or 4 and n is 2 or 3, reacting a piperidyl compound of formula (III)

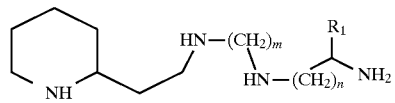

wherein
R$_1$ is hydrogen and
n and m are as defined for compounds of formula (I), with a compound of fornula (IV)

R$_2$'—X    (IV)

wherein
R$_2$' is lower alkyl, lower alkenyl or lower alkynyl and
X is a nucleofugal leaving group;
primary and secondary amino groups in the compound of formula (III) each being in monoprotected form;
and removing any protecting groups that are present; or
c) reacting a piperidyl compound of formula (V)

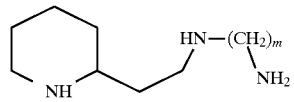

wherein
m is 3 or 4, with a compound of formula (VI)

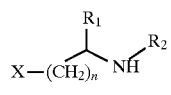

wherein
R$_1$, R$_2$ and n are as defined for compounds of formula (I) and

X is a nucleofugal leaving group;
primary and secondary amino groups in the compounds of formula (V) and formula (VI) each being in monoprotected form;
and removing any protecting groups that are present; or
d) reacting a piperidyl compound of formula (VII)

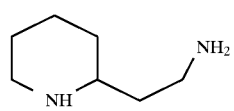

with a compound of formula (VIII)

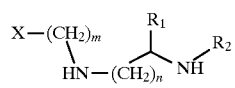

wherein
R$_1$, R$_2$, m and n are as defined for compounds of formula (I);
primary and secondary amino groups in the compounds of formula (VII) and formula (VIII) each being in monoprotected form;
and removing any protecting, groups that are present;
it being possible for the starting materials in processes a) to d) to be in the form of their salts, provided that salt-forming groups are present;
and, if desired, converting an obtainable salt of a compound of formula (I) into the free compound or into a different salt of a compound of formula (I), converting an obtainable free compound of formula (I) into its salt, and/or separating obtainable mixtures of isomers into isomers.

11. A pharmaceutical composition comprising a pharmaceutically acceptable carrier or diluent and a therapeutically effective amount of a compound according to claim 1, or a pharmaceutically acceptable salt thereof.

12. A method of treating pathological conditions which are responsive to a reduction in the intracellular concentration of polyamines comprising administering to a subject in need of such treatment a therapeutically effective amount of a compound according to claim 1, or a pharmaceutically acceptable salt thereof.

13. A method according to claim 12 for treating a proliferative disease.

14. A method according lo claim 12 for treating a protozoal infection.

* * * * *